(12) United States Patent  
Cho et al.

(10) Patent No.: US 8,115,019 B2
(45) Date of Patent: Feb. 14, 2012

(54) CIS-2, 6-DISUBSTITUTED TETRAHYDROPYRAN DERIVATIVES AND PREPARATION METHOD THEREOF

(75) Inventors: Yong Seo Cho, Seoul (KR); You Seung Kim, Seoul (KR); Jae Kyun Lee, Seoul (KR); Hyunah Choo, Seoul (KR); Ae Nim Pae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 668 days.

(21) Appl. No.: 12/243,244

(22) Filed: Oct. 1, 2008

(65) Prior Publication Data

US 2009/0209770 A1    Aug. 20, 2009

(30) Foreign Application Priority Data

Feb. 20, 2008 (KR) .................. 10-2008-0015550

(51) Int. Cl.
 *C07D 309/06* (2006.01)
 *C07D 309/22* (2006.01)
(52) U.S. Cl. .................. 549/425; 549/426; 549/427
(58) Field of Classification Search .................. 549/425, 549/426, 427
See application file for complete search history.

(56) References Cited

OTHER PUBLICATIONS

Arun K.Ghosh, et al. "Enantioselective Total Synthesis of Macrolide Antitumor Agent (−)-Lasonolide A", Organic Letters 2007, vol. 9, No. 8, pp. 1437-1440.
Richard E. Moore, et al. "Structure of Palytoxin", J. Am. Chem. Soc. 1981, 103, 2497-2494.

*Primary Examiner* — Bernard Dentz
(74) *Attorney, Agent, or Firm* — Lang & Parry LLP

(57) ABSTRACT

Disclosed are cis-2,6-disubstituted tetrahydropyran derivatives represented by Chemical Formula 1 and a preparation method thereof. The tetrahydropyran derivatives can be prepared by Prins-reacting tetrahydropyran derivatives with homopargylicalcohol derivatives in the presence of trimethylsilyltriflate. The tetrahydropyran derivatives with cis-substituents at both C2 and C6 positions of the tetrahydropyran ring are useful as intermediates for use in the synthesis and development of therapeutically effective, naturally occurring compounds.

[Chemical Formula 1]

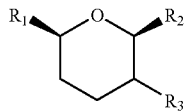

(wherein, $R_1$, $R_2$ and $R_3$ are as defined in the specification.).

10 Claims, No Drawings

CIS-2, 6-DISUBSTITUTED TETRAHYDROPYRAN DERIVATIVES AND PREPARATION METHOD THEREOF

BACKGROUND OF THE INVENTION

1. Field of the Invention

The present invention relates to cis-2,6-disubstituted tetrahydropyran derivatives and a method for the preparation thereof.

2. Description of the Related Art

Of the naturally occurring materials which are therapeutically effective, many are based on a stereoselective tetrahydropyran structure with cis-substituents at both C2 and C6 positions, or all of C2, C3 and C6 positions [Org. Lett. 2007, 9, 1437-1440; JACS. 1981, 103, 2491-2494].

Thus, the novel compounds of the present invention, which have not been mentioned previously, are based on a tetrahydropyran moiety with cis-substituents at both C2 and C6 positions or all of C2, C3 and C6 positions, and thus can be useful as intermediates for use in the synthesis and development of therapeutically effective, novel drugs of high stereoselectivity.

SUMMARY OF THE INVENTION

It is therefore an object to provide novel cis-2,6-disubstituted tetrahydropyran derivatives.

It is another object to provide a method for preparing the novel tetrahydropyran derivatives.

In order to accomplish the object, the present invention provides a cis-2,6-disubstituted tetrahydropyran derivative, represented by the following chemical formula 1:

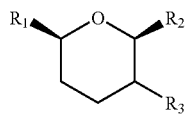

[Chemical Formula 1]

wherein, $R_1$ and $R_2$ independently represent a $C_1$-$C_6$ alkyl, a $C_6$-$C_{15}$ aryl $C_1$-$C_6$ alkyl, or a $C_6$-$C_{15}$ aryl, said aryl being non-substituted or substituted with one to four substituents selected from a group consisting of a halogen, a nitro and a $C_1$-$C_6$ alkyl; and $R_3$ is methylidene ethyltriflate or acetoxy.

Also, the present invention provides a method for preparing the cis-2,6-substituted tetrahydropyran derivative, comprising the Prins reaction of a homopropargylic alcohol derivative with an aldehyde compound in the presence of a Lewis acid.

According to the present invention, the tetrahydropyran compounds, represented by Chemical Formula 1, which is based on a tetrahydropyran moiety with two or more cis-substituents, can be useful as intermediates for use in the synthesis and development of therapeutically effective, novel drugs of high stereoselectivity. Also, they can be easily prepared using the preparation method according to the present invention.

DESCRIPTION OF THE PREFERRED EMBODIMENTS

In accordance with an aspect thereof, the present invention pertains to tetrahydropyran derivatives, represented by the following chemical formula 1:

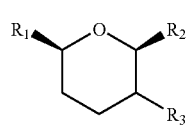

[Chemical Formula 1]

wherein, $R_1$ and $R_2$ independently represent a $C_1$-$C_6$ alkyl group, $C_6$-$C_{15}$ aryl $C_1$-$C_6$ alkyl group, or a $C_6$-$C_{15}$ aryl group, the aryl moiety being non-substituted or substituted with one to four substituents selected from a group consisting of a halogen, a nitro, and a $C_1$-$C_6$ alkyl; and $R_3$ is methylidene ethyltriflate or acetoxy.

As used herein, the term "alkyl" is intended to refer to a straight or branched chain containing 1 to 6 carbon atoms. Examples include methyl, ethyl, n-propyl, isopropyl, n-butyl, isobutyl, t-butyl, n-pentyl and n-hexyl.

The term "aryl", as used herein, is intended to denote any functional group or substituent derived from one or more planar sets of six carbon atoms that are connected by delocalized electrons numbering the same as if they consisted of alternating single and double covalent bonds, be it phenyl, naphthyl, etc.

The term "arylalkyl", as used herein, denotes that the aryl defined above is linked to an alkyl, be it benzyl, phenylethyl, phenylpropyl, naphthylmethyl, naphthylethyl, etc. One to four substituents, such as halogen atoms, a C1-C6 alkyl, a nitro, etc., may be present on the aromatic rings of the aryl or arylalkyl.

In greater detail, the tetrahydropyran derivatives according to the present invention may be represented by the following chemical formula 1a or 1b:

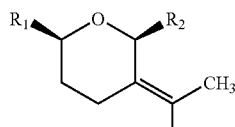

(1a)

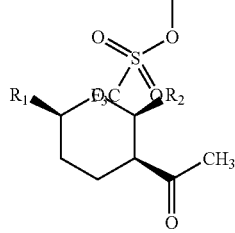

(1b)

The tetrahydropyran derivatives of Chemical Formula 1a have cis-substituents at both C2 and C6 positions while three cis-substituents are present at positions C2, C3 and C6 on the tetrahydropyran derivatives of Chemical Formula 1b, which may be derived from the compounds of Chemical Formula 1a through hydrolysis.

Representative examples of the tetrahydropyran derivatives represented by Chemical Formula 1 include:

(1) (E)-1-((2S,6S)-2-(4-nitrophenyl)-6-phenyl-dihydro-2H-pyran-3(4H)-ylidene)-ethyl trifluoromethanesulfonate;

(2) (E)-1-(2,6-diphenyl-dihydro-2H-pyran-3(4H)-ylidene)-ethyl trifluoromethanesulfonate;

(3) (E)-1-(2-(naphthalen-2-yl)-6-phenyl-dihydro-2H-pyran-3(4H)-ylidene)-ethyl trifluoromethanesulfonate;

(4) (E)-(2-(4-chlorophenyl)-6-phenyl-dihydro-2H-pyran-3(4H)-ylidene)-ethyl trifluoromethanesulfonate;

(5) (E)-(2-(4-nitrophenyl)-6-phenyl-dihydro-2H-pyran-3(4H)-ylidene)-ethyl trifluoromethanesulfonate;

(6) (E)-1-(2-methyl-6-phenyl-dihydro-2H-pyran-3(4H)-ylidene)-ethyl trifluoromethanesulfonate;

(7) (E)-1-((2S,6R)-2,6-methyl-dihydro-2H-pyran-3(4H)-ylidene)-ethyl trifluoromethanesulfonate;

(8) (E)-1-(2-ethyl-6-phenyl-dihydro-2H-pyran-3(4H)-ylidene)-ethyl trifluoromethanesulfonate;

(9) (E)-1-(2-isopropyl-6-phenyl-dihydro-2H-pyran-3(4H)-ylidene)-ethyl trifluoromethanesulfonate;

(10) (E)-1-(2-pentyl-6-phenyl-dihydro-2H-pyran-3(4H)-ylidene)-ethyl trifluoromethanesulfonate;

(11) (E)-1-(2-phenylethyl-6-phenyl-dihydro-2H-pyran-3(4H)-ylidene)-ethyl trifluoromethanesulfonate; and

(12) 1-((2R,3R,6S)-2-(4-nitrophenyl)-6-phenyl-tetrahydro-2H-pyran-3-yl)ethanone.

In accordance with another aspect thereof, the present invention pertains to a method for preparing the tetrahydropyran derivatives, as illustrated by the following Reaction Scheme 1, by reacting homopropargylic alcohol derivatives 2 with aldehyde compounds 3 in the presence of a Lewis acid:

[Reaction Scheme 1]

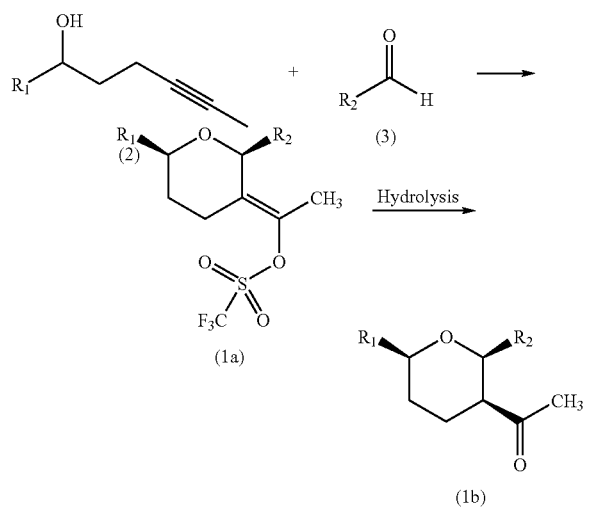

wherein $R_1$ and $R_2$ are as defined in Chemical Formula 1, and Compounds 1a and 1b fall within the range of the compounds of Chemical Formula 1.

In the first step of Reaction Scheme 1, a homopropargylic alcohol derivative represented by Chemical Formula 2 and an aldehyde compound represented by Chemical Formula 3 are subjected to a Prins reaction in the presence of a Lewis acid to afford a dihydropyran-3-ylidene triflate compound represented by Chemical Formula 1a.

Preferable as a Lewis acid for use in the Prins reaction is trimethylsilyltrifluoromethanesulfonate (TMSOTf). The Lewis acid is used in an amount from 1 to 4 equivalents based on the equivalent of the homopropargylic alcohol derivative of Chemical Formula 2 and preferably in an amount from 2.5 to 3.5 equivalents. The solvent useful in the Prins reaction may be a typical organic one and may preferably be dichloromethane. During the Prins reaction, reaction temperature may be preferably maintained within a range from −78° C. to 30° C.; the Prins reaction may be well conducted at room temperature. The reaction is preferably conducted over 3 to 5 hours.

The method according to the present invention may further comprise, as illustrated in Reaction Scheme 1, hydrolyzing the dihydropyran-3-ylidene triflate compound represented by Chemical Formula 1a into a tetrahydropyran compound represented by Chemical Formula 1b.

This hydrolysis reaction is typically conducted in an acid or alkali condition. The same typical organic solvent as used in the Prins reaction may be used, and preferably dichloromethane. For the hydrolysis reaction, the reaction temperature is maintained within a range from 0 to 30° C. Likewise, the hydrolysis is well conducted at room temperature. A time period of from 1 to 3 hours is preferably given for the hydrolysis reaction.

In cooperation with a Prins reaction, as described above, the orientation of the starting material determines the configuration of the 2,6-disubstituted tetrahydropyran derivatives such as cis-2,6-dihydropyran-3-ylidene triflate compounds, and their hydrolysates such as cis-2,3,6-tetrahydropyran derivatives. In addition, the Prins cyclization of the present invention is relatively simple and highly stereoselective, and requires such mild reaction conditions that it can be used for synthesizing chiral compounds. Therefore, the tetrahydropyran derivatives of the present invention find useful applications in the medical industry and the fine chemical industry, where they are useful as intermediates for use in the synthesis and development of therapeutically effective, novel drugs of high stereoselectivity.

A better understanding of the present invention may be obtained through the following examples which are set forth to illustrate, but are not to be construed as limiting the present invention.

EXAMPLES

Example 1

Synthesis of (E)-1-((2S,6S)-2-(4-nitrophenyl)-6-phenyl-dihydro-2H-pyran-3(4H)-ylidene)-ethyltrifluoromethanesulfonate

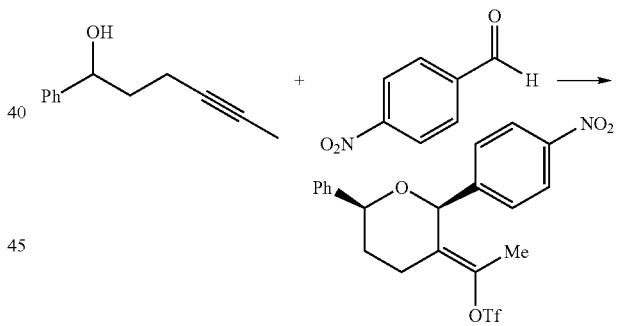

In dichloromethane (3.0 mL) were dissolved 1-phenylhex-4-yn-1-ol (0.28 mmol) and 4-nitrobenzaldehyde (0.34 mmol) and the solution was cooled to −78° C. before the addition of trimethylsilyltriflate (TMSOTf) (0.86 mmol) thereto. After being stirred for 1 hour at the same temperature, the reaction solution was slowly heated to room temperature over 3 hours. Stirring was further conducted at room temperature for an additional one to two hours in the reaction solution. After the addition of an aqueous $NaHCO_3$ solution, the reaction solution was diluted with diethylether. The organic layer was washed with water and brine, dried over $MgSO_4$, filtered and concentrated. The purification of the concentrate through column chromatography afforded the title compound (Yield 82%).

$^1$H NMR (400 MHz, $CDCl_3$) δ 8.26 (d, 2H, J=4.3 Hz), 7.66 (d, 2H, J=4.3 Hz), 7.30-7.39 (m, 5H), 5.60 (s, 1H), 4.69 (dd, 1H, J=10.6, 5.2 Hz), 2.88-2.93(m, 1H), 2.49-2.52 (m, 1H), 2.15-2.19 (m, 1H), 2.05-2.08 (m, 1H), 1.99 (s, 3H); $^{13}$C NMR (100 MHz, CDCl3) δ 147.81, 146.33, 141.87, 141.76, 130.51, 128.56, 127.86, 125.72, 123.97, 123.12, 119.93, 116.76, 113.58, 77.37, 76.15, 31.50, 21.82, 17.30

Example 2

Synthesis of (E)-1-(2,6-Diphenyl-dihydro-2H-pyran-3(4H)-ylidene)-ethyltrifluoromethanesulfonate

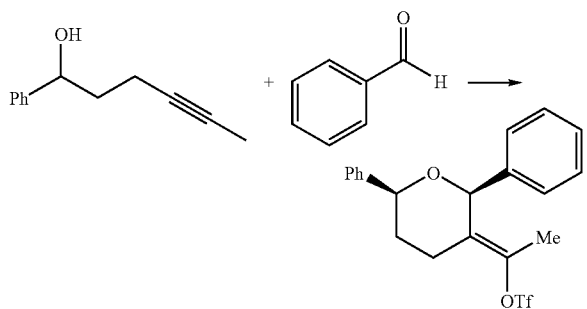

In dichloromethane (3.0 mL) were dissolved 1-phenylhex-4-yn-1-ol (0.28 mmol) and benzaldehyde (0.34 mmol) and the solution was cooled to −78° C. before the addition of trimethylsilyltriflate (TMSOTf) (0.86 mmol) thereto. At the same temperature, the reaction solution was stirred for 1 hour, and then slowly heated to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 79%).

$^1$H NMR (400 MHz, CDCl$_3$) δ 7.36-7.51 (m, 10H), 5.50 (s, 1H), 4.68 (dd, 1H, J=10.4, 5.2 Hz), 2.88-2.90 (m, 1H), 2.65-2.69 (m, 1H), 2.16-2.20 (m, 1H), 2.06-2.10 (m, 1H); $^{13}$C NMR (100 MHz, CDCl3) δ 142.48, 141.43, 131.03, 128.76, 128.44, 128.37, 127.70, 127.53, 127.13, 125.76, 120.00, 116.82, 113.58, 78.53, 76.15, 31.84, 30.35, 22.30, 17.19

Example 3

Synthesis of (E)-1-(2-(naphthalen-2-yl)-6-phenyl-dihydro-2H-pyran-3(4H)-ylidene)-ethyl trifluoromethanesulfonate

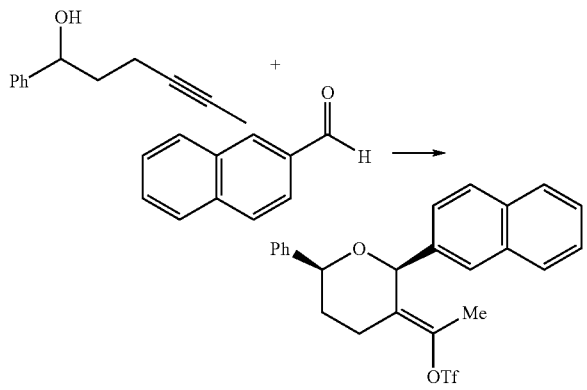

In dichloromethane (3.0 mL) were dissolved 1-phenylhex-4-yn-1-ol (0.28 mmol) and 2-naphthalenealdehyde (0.34 mmol) and the solution was cooled to −78° C. before the addition of trimethylsilyltriflate (TMSOTf) (0.86 mmol) thereto. After being stirred for 1 hour at the same temperature, the reaction solution was slowly heated to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 81%).

$^1$H NMR (400 MHz, CDCl$_3$) δ 7.86-7.90 (m, 4H), 7.71-7.73 (d, 1H), 7.51-7.53 (m, 2H), 7.29-7.43 (m, 5H), 5.64 (s, 1H), 4.72 (dd, 1H, J=10.4, 5.4 Hz), 2.91-2.94 (m, 1H), 2.67-2.70 (m, 1H), 2.18-2.21 (m, 1H), 2.06-2.12 (m, 1H), 1.91 (s, 1H); $^{13}$C NMR (100 MHz, CDCl3) δ 142.47, 141.56, 136.51, 133.23, 130.89, 128.65, 128.45, 128.28, 127.67, 127.55, 126.36, 126.32, 126.06, 125.77, 125.16, 123.17, 119.99, 116.82, 113.64, 78.63, 76.26, 31.73, 22.36, 17.27

Example 4

Synthesis of (E)-(2-(4-chlorophenyl)-6-phenyl-dihydro-2H-pyran-3(4H)-ylidene)-ethyl trifluoromethanesulfonate

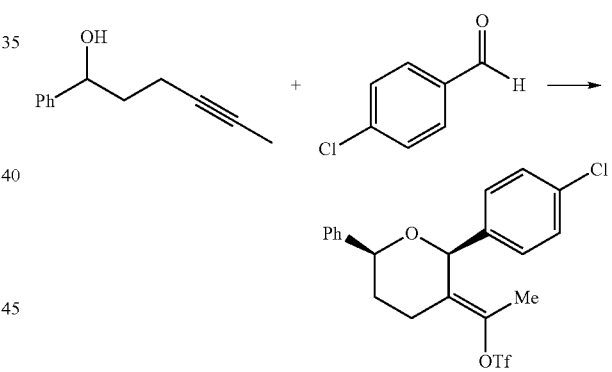

In dichloromethane (3.0 mL) were dissolved 1-phenylhex-4-yn-1-ol (0.28 mmol) and 4-chlorobenzaldehyde (0.34 mmol) and the solution was cooled to −78° C. before the addition of trimethylsilyltriflate (TMSOTf) (0.86 mmol) thereto. After being stirred for 1 hour at the same temperature, the reaction solution was slowly heated to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 78%).

$^1$H NMR (400 MHz, CDCl$_3$) δ 7.28-7.41 (m, 10H), 5.45 (s, 1H), 4.65 (dd, 1H, J=10.5, 5.4 Hz), 2.83-2.86 (m, 1H), 2.51-2.59 (m, 1H), 2.12-2.18 (m, 1H), 2.02-2.07 (m, 1H), 1.89 (s, 1H); $^{13}$C NMR (75 MHz, CDCl3) δ 142.19, 141.44, 137.12, 134.20, 130.69, 128.93, 128.46, 127.62, 125.70, 124.70, 120.46, 116.23, 111.99, 77.73, 76.11, 31.60, 22.06, 17.21

Example 5

Synthesis of (E)-(2-(4-nitrophenyl)-6-phenyl-dihydro-2H-pyran-3(4H)-ylidene)-ethyl trifluoromethanesulfonate

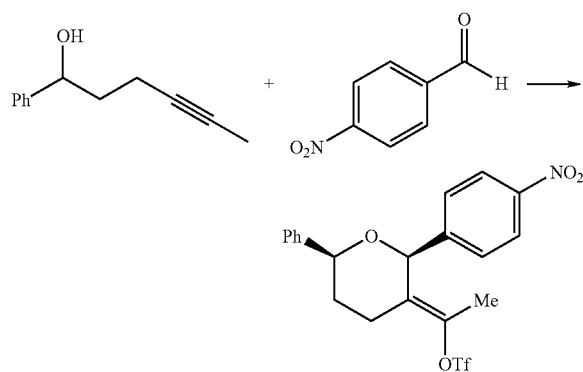

In dichloromethane (3.0 mL) were dissolved 1-phenylhex-4-yn-1-ol (0.28 mmol) and 2-naphthalenealdehyde (0.34 mmol) and the solution was cooled to −78° C. before the addition of trimethylsilyltriflate (TMSOTf) (0.86 mmol) thereto. At the same temperature, the reaction solution was stirred for 1 hour, and then slowly heated to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 78%).

$^1$H NMR (400 MHz, CDCl$_3$) δ 7.92 (d, 1H, J=8.0 Hz), 7.73 (d, 1H, J=7.7 Hz), 7.65 (d, 1H, J=7.4 Hz), 7.52 (d, 1H, J=7.7 Hz), 7.21-7.35 (m, 5H), 5.98 (s, 1H), 4.70 (dd, 1H, J=10.6, 4.7 Hz), 2.78-2.81 (m, 2H), 2.17-2.22 (m, 1H), 1.99-2.05 (m, 1H), 1.66 (s, 3H); $^{13}$C NMR (100 MHz, CDCl3) δ 149.34, 141.83, 141.61, 133.30, 129.59, 129.46, 128.81, 128.43, 127.63, 125.53, 124.70, 123.13, 119.95, 116.78, 113.60, 78.00, 75.10, 32.23, 24.72, 17.20

Example 6

Synthesis of (E)-1-(2-methyl-6-phenyl-dihydro-2H-pyran-3(4H)-ylidene)-ethyl trifluoromethanesulfonate

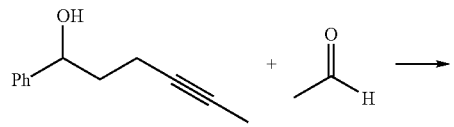

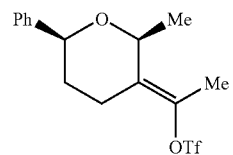

In dichloromethane (3.0 mL) were dissolved 1-phenylhex-4-yn-1-ol (0.28 mmol) and ethanal (0.34 mmol) and the solution was cooled to −78° C. before the addition of trimethylsilyltriflate (TMSOTf) (0.86 mmol) thereto. At the same temperature, the reaction solution was stirred for 1 hour, followed by slow temperature elevation to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 76%).

$^1$H NMR (400 MHz, CDCl$_3$) δ 7.32-7.37 (m, 4H), 7.26-7.29 (m, 1H), 4.59 (q, 1H, J=6.4 Hz), 4.38 (dd, 1H, J=10.2, 6.3 Hz), 2.74-2.80 (m, 1H), 2.36-2.44 (m, 1H), 2.01-2.10 (m, 5H), 1.40-1.41 (d, 3H, J=6.4 Hz)

Example 7

Synthesis of (E)-1-((2S,6R)-2,6-Dimethyl-dihydro-2H-pyran-3(4H)-ylidene)-ethyl trifluoromethanesulfonate

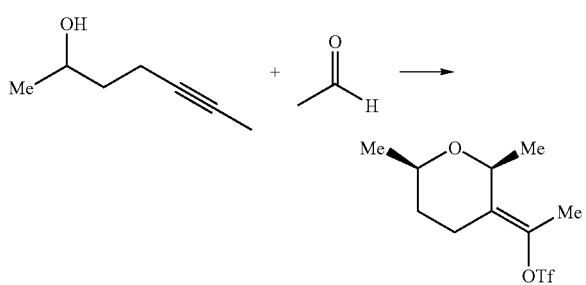

In dichloromethane (3.0 mL) were dissolved hept-5-yn-2-ol (0.28 mmol) and acetaldehyde (0.34 mmol) and the solution was cooled to −78° C. before the addition of trimethylsilyltriflate (TMSOTf) (0.86 mmol) thereto. At the same temperature, the reaction solution was stirred for 1 hour, followed by slow temperature elevation to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 72%).

1H NMR (400 MHz, CDCl$_3$) δ 4.54 (q, 1H, J=6.4 Hz), 3.70 (q, 1H, J=6.4 Hz), 2.74-2.80 (m, 1H), 2.36-2.44 (m, 1H), 2.01-2.10 (m, 5H), 1.40-1.41 (d, 6H, J=6.4 Hz)

Example 8

Synthesis of (E)-1-(2-ethyl-6-phenyl-dihydro-2H-pyran-3(4H)-ylidene)-ethyl trifluoromethane-sulfonate

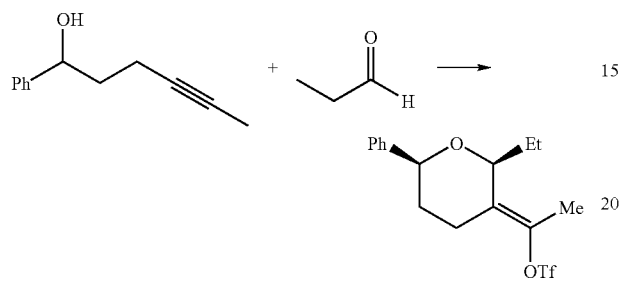

In dichloromethane (3.0 mL) were dissolved 1-phenylhex-4-yn-1-ol (0.28 mmol) and propionaldehyde (0.34 mmol) and the solution was cooled to −78° C. before the addition of trimethylsilyltriflate (TMSOTf) (0.86 mmol) thereto. At the same temperature, the reaction solution was stirred for 1 hour, and then slowly heated to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 77%).

$^1$H NMR (400 MHz, CDCl$_3$) δ 7.24-7.39 (m, 5H), 4.37-4.48 (m, 2H), 2.78-2.83 (m, 1H), 2.41-2.50 (m, 1H), 1.98-2.08 (m, 5H), 1.80-1.85 (m, 1H), 1.65-1.73 (m, 1H), 1.04-1.08 (t, 3H)

Example 9

Synthesis of (E)-1-(2-isopropyl-6-phenyl-dihydro-2H-pyran-3(4H)-ylidene)-ethyl trifluoromethane-sulfonate

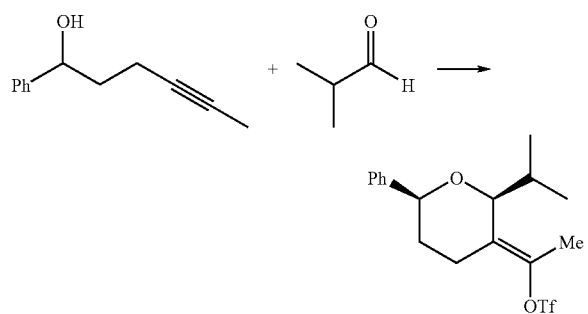

In dichloromethane (3.0 mL) were dissolved 1-phenylhex-4-yn-1-ol (0.28 mmol) and isobudylaldehyde (0.34 mmol) and the solution was cooled to −78° C. before the addition of trimethylsilyltriflate (TMSOTf) (0.86 mmol) thereto. At the same temperature, the reaction solution was stirred for 1 hour, followed by slow temperature elevation to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 75%).

$^1$HNMR (400 MHz, CDCl$_3$) δ 7.25-7.37 (m, 5H), 4.40 (dd, 1H, J=10.6, 5.6 Hz), 4.24 (d, 1H, J=5.9 Hz), 2.82-2.85 (m, 1H), 2.28-2.37 (m, 1H), 1.95-2.11 (m, 6H), 1.14 (d, 3H, J=6.6 Hz), 1.03 (d, 3H, J=10.6 Hz)

Example 10

Synthesis of (E)-1-(2-Pentyl-6-phenyl-dihydro-2H-pyran-3(4H)-ylidene)-ethyl trifluoromethane-sulfonate

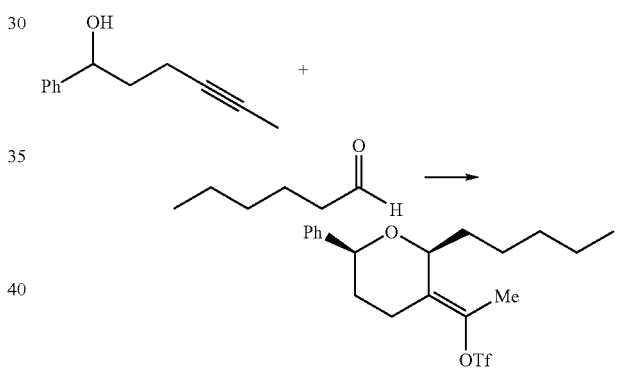

In dichloromethane (3.0 mL) were dissolved 1-phenylhex-4-yn-1-ol (0.28 mmol) and hexanal (0.34 mmol) and the solution was cooled to −78° C. before the addition of trimethylsilyltriflate (TMSOTf) (0.86 mmol) thereto. At the same temperature, the reaction solution was stirred for 1 hour, followed by slow temperature elevation to room temperature over 3 hours. Stirring was further conducted at room temperature for an additional one to two hours in the reaction solution. After the addition of an aqueous NaHCO$_3$ solution, the reaction solution was diluted with diethylether. The organic layer was washed with water and brine, dried over MgSO$_4$, filtered and concentrated. The purification of the concentrate through column chromatography afforded the title compound (Yield 76%).

$^1$H NMR (400 MHz, CDCl$_3$) δ 7.33-7.37 (m, 4H), 7.24-7.29 (m, 1H), 4.46 (dd, 1H, J=7.6, 2.6 Hz), 4.38 (m, 1H, J=10.5, 6.0 Hz), 2.77-2.79 (m, 1H), 2.30-2.38 (m, 1H), 1.98-2.09 (m, 5H), 1.79-1.84 (m, 1H), 1.54-1.59 (m, 4H), 1.34-1.37 (m, 4H), 0.90-0.93 (t, 3H)

Example 11

Synthesis of (E)-1-(2-Phenylethyl-6-phenyl-dihydro-2H-pyran-3(4H)-ylidene)-ethyl trifluoromethanesulfonate

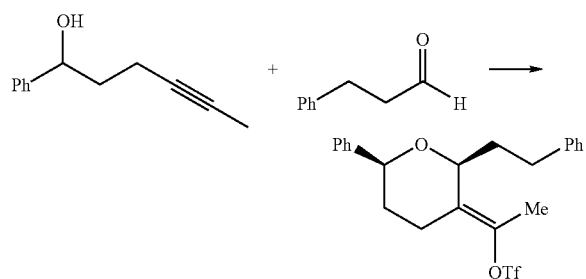

In dichloromethane (3.0 mL) were dissolved 1-phenylhex-4-yn-1-ol (0.28 mmol) and phenylpropanal (0.34 mmol) and the solution was cooled to −78° C. before the addition of trimethylsilyltriflate (TMSOTf) (0.86 mmol) thereto. At the same temperature, the reaction solution was stirred for 1 hour, followed by slow temperature elevation to room temperature over 3 hours. Stirring was further conducted at room temperature for an additional one to two hours in the reaction solution. After the addition of an aqueous $NaHCO_3$ solution, the reaction solution was diluted with diethylether. The organic layer was washed with water and brine, dried over $MgSO_4$, filtered and concentrated. The purification of the concentrate through column chromatography afforded the title compound (Yield 69%).

$^1$HNMR (400 MHz, $CDCl_3$) δ 7.37-7.39 (m, 4H), 7.28-7.32 (m, 3H), 7.19-7.24 (m, 3H), 4.38-4.44 (m, 2H), 2.79-2.91 (m, 3H), 2.34-2.43 (m, 1H), 2.0-2.17 (m, 3H), 1.93-1.94 (s, 3H), 1.90-1.92 (m, 1H)

Example 12

Synthesis of 1-((2R,3R,6S)-2-(4-Nitrophenyl)-6-phenyl-tetrahydro-2H-pyran-3-yl)ethanol

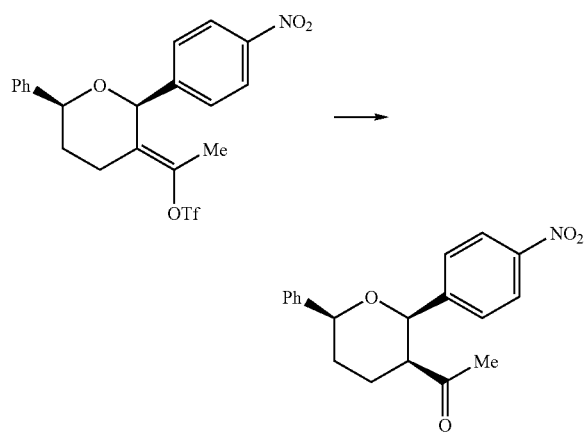

A solution of (E)-(2-(4-nitrophenyl)-6-phenyl-dihydro-2H-pyran-3(4H)-ylidene)ethyl trifluoromethanesulfonate (0.3 mmol) in a mixture of 2:1 1,4-dioxane:methanol was treated with an aqueous NaOH solution (1%, 4 mL) at room temperature for 3 hours with stirring. Following completion of the reaction, brine was added to the reaction solution which was then diluted with ethylacetate. The organic layer thus formed was washed with water, dried over $Na_2SO_4$, filtered and concentrated. The purification of the concentrate afforded the title compound (Yield 75%).

$^1$H NMR (400 MHz, $CDCl_3$) δ 8.18 (d, 2H, J=8.7 Hz), 7.58 (d, 2H, J=8.7 Hz), 7.27-7.43 (m, 7H), 4.84 (d, 1H, J=9.9 Hz), 4.61 (d, 1H, J=11.2 Hz), 2.86-2.90 (m, 1H), 2.11-2.25 (m, 1H), 1.98-2.10 (m, 2H), 1.87 (s, 3H), 1.74-1.82 (m, 1H)

Based on a tetrahydropyran moiety with two or more cis-substituents, as described hitherto, the tetrahydropyran compounds, represented by Chemical Formula 1, according to the present invention can be useful as intermediates for use in the synthesis and development of therapeutically effective, novel drugs of high stereoselectivity. Also, they can be easily prepared using the preparation method according to the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A tetrahydropyran compound with cis-substituents at C2 and C6 positions, represented by the following Chemical Formula 1:

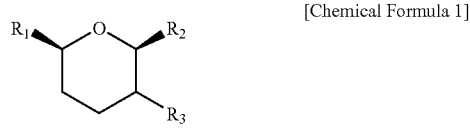

[Chemical Formula 1]

wherein the bond between R3 and the carbon of the ring is either single or double, $R_1$ and $R_2$ independently represent a $C_1$-$C_6$ alkyl group, a $C_6$-$C_{15}$ aryl $C_1$-$C_6$ alkyl group, or a $C_6$-$C_{15}$ aryl group, the aryl moiety being non-substituted or substituted with one to four substituents selected from a group consisting of a halogen, a nitro, and a $C_1$-$C_6$ alkyl; and $R_3$ is acetyl which is attached to the carbon of the ring by a single bond or ethylidene triflate which is attached to the carbon of the ring by a double bond.

2. The tetrahydropyran compound as set forth in claim 1, wherein the compound has two cis-substituents at positions C2 and C6 as is represented by the following Chemical Formula 1a:

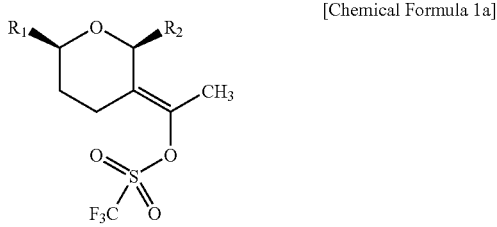

[Chemical Formula 1a]

wherein, R1 and R2 are as defined in claim 1.

3. The tetrahydropyran compound as set forth in claim 1, wherein the compound has three cis-substituents at positions C2, C3 and C6 as is represented by the following Chemical Formula 1b:

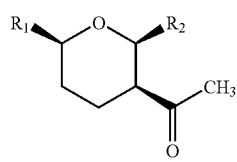

[Chemical Formula 1b]

wherein, $R_1$ and $R_2$ are as defined in claim 1.

4. The tetrahydropyran compound as set forth in claim 1, selected from a group consisting of:
   (1) (E)-1-((2S,6S)-2-(4-nitrophenyl)-6-phenyl-dihydro-2H-pyran-3 (4H)-ylidene) -ethyltrifluoromethanesulfonate;
   (2) (E)-1-(2,6-diphenyl-dihydro-2H-pyran-3(4H)-ylidene) -ethyltrifluoromethanesulfonate;
   (3) (E)-1-(2-(naphthalen-2-yl)-6-phenyl-dihydro-2H-pyran-3(4H)-ylidene)-ethyl trifluoromethanesulfonate;
   (4) (E)-(2-(4-chlorophenyl)-6-phenyl-dihydro-2H-pyran-3(4H)-ylidene)-ethyl trifluoromethanesulfonate;
   (5) (E)-(2-(4-nitrophenyl)-6-phenyl-dihydro-2H-pyran-3 (4H)-ylidene)-ethyl trifluoromethanesulfonate;
   (6) (E)-1-(2-methyl-6-phenyl-dihydro-2H-pyran-3(4H)-ylidene)-ethyl trifluoromethanesulfonate;
   (7) (E)-1-((2S,6R)-2,6-dimethyl-dihydro-2H-pyran-3 (4H)-iylidene)-ethyl trifluoromethanesulfonate;
   (8) (E)-1-(2-ethyl-6-phenyl-dihydro-2H-pyran-3(4H)-ylidene)-ethyl trifluoromethanesulfonate;
   (9) (E)-1-(2-isopropyl-6-phenyl-dihydro-2H-pyran-3 (4H)-ylidene)-ethyl trifluoromethanesulfonate;
   (10) (E)-1-(2-pentyl-6-phenyl-dihydro-2H-pyran-3(4H)-ylidene)-ethyl trifluoromethanesulfonate;
   (11) (E)-1-(2-phenylethyl-6-phenyl-dihydro-2H-pyran-3 (4H)-ylidene)-ethyl trifluoromethanesulfonate; and
   (12) 1-((2R,3R,6S)-2-(4-nitrophenyl)-6-phenyl-tetrahydro-2H-pyran-3-yl) ethanone.

5. A method for preparing the tetrahydropyran compound of claim 1, comprising subjecting a homopropargylic alcohol derivative, represented by the following Chemical Formula 2, and an aldehyde compound, represented by the following Chemical Formula 3, to a Prins reaction in a presence of a Lewis acid to synthesize a dihydropyran-3-ylidene triflate compound, represented by the following Chemical Formula 1 a:

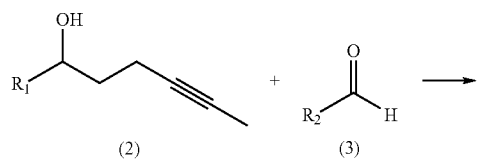

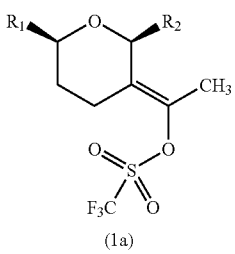

(1a)

wherein, $R_1$ and $R_2$ are as defined in claim 1, and the compound of Chemical Formula 1a falls within the range of the compound of Chemical Formula 1.

6. The method as set forth in claim 5, further comprising hydrolyzing the dihydropyran-3-ylidene triflate, represented by Chemical Formula 1a, into a tetrahydropyran compound, represented by the following Chemical Formula 1b:

[Reaction Scheme 1]

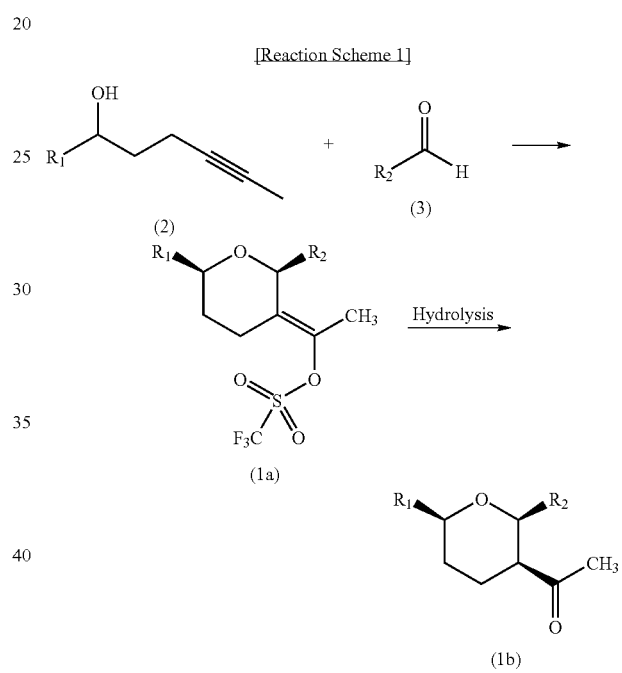

wherein, $R_1$ and $R_2$ are as defined in claim 1, and the compounds of Chemical Formulas 1a and 1b are included within the range of the compound of Chemical Formula 1.

7. The method as set forth in claim 5, wherein the Lewis acid is trimethylsilyl trifluoromethanesulfonate (TMSOTf).

8. The method as set forth in claim 7, wherein the trimethylsilyl trifluoromethanesulfonate (TMSOTf) is used in an amount of 2.5 to 3.5 equivalents per equivalent of the homopropargylic alcohol derivative represented by Chemical Formula 2.

9. The method as set forth in claim 5, wherein the Prins reaction is conducted at a temperature range of from −78° C. to 30° C.

10. The method as set forth in claim 5, wherein the Prins reaction is conducted in dichloromethane as a solvent.

* * * * *